United States Patent
Ge et al.

(10) Patent No.: US 10,487,301 B2
(45) Date of Patent: Nov. 26, 2019

(54) REACTION TUBE FOR NUCLEIC ACID AMPLIFICATION CAPABLE OF CONTROLLING LIQUID CIRCULATION PATH

(71) Applicants: XIAMEN UNIVERSITY, Xiamen (CN); XIAMEN INNODX BIOTECH CO., LTD, Xiamen (CN)

(72) Inventors: Shengxiang Ge, Xiamen (CN); Shiyin Zhang, Xiamen (CN); Feihai Xu, Xiamen (CN); Jin Wang, Xiamen (CN); Jinjie Li, Xiamen (CN); Jun Zhang, Xiamen (CN); Ningshao Xia, Xiamen (CN)

(73) Assignees: XIAMEN UNIVERSITY, Xiamen (CN); XIAMEN INNODX BIOTECH CO., LTD., Xiamen (CN)

( * ) Notice: Subject to any disclaimer, the term of this patent is extended or adjusted under 35 U.S.C. 154(b) by 57 days.

(21) Appl. No.: 15/573,381

(22) PCT Filed: May 11, 2016

(86) PCT No.: PCT/CN2016/081649
§ 371 (c)(1),
(2) Date: Nov. 10, 2017

(87) PCT Pub. No.: WO2016/180333
PCT Pub. Date: Nov. 17, 2016

(65) Prior Publication Data
US 2019/0055506 A1    Feb. 21, 2019

(30) Foreign Application Priority Data
May 12, 2015    (CN) ........................ 2015 1 0237018

(51) Int. Cl.
C12M 1/38    (2006.01)
C12M 1/24    (2006.01)
(Continued)

(52) U.S. Cl.
CPC ............. C12M 1/38 (2013.01); B01L 3/5082 (2013.01); B01L 3/50273 (2013.01);
(Continued)

(58) Field of Classification Search
CPC ................ C12M 1/38; B01L 3/502753; B01L 2300/1805; B01L 2400/0445; C12Q 1/6844
See application file for complete search history.

(56) References Cited

U.S. PATENT DOCUMENTS 6,649,378 B1 * 11/2003 Kozwich ................ B01L 3/502
                                                             422/68.1
7,628,961 B2    12/2009 Hwang et al.
(Continued)

FOREIGN PATENT DOCUMENTS

CA    2856345    *    5/2013
CN    1571849 A         1/2005
(Continued)

OTHER PUBLICATIONS

Zhang et al (Post art), An efficient isothermal PCR method for on-site detection of nucleic acid, 2019, BioTechniques, 67, pp. 1-7 (Year: 2019).*
(Continued)

Primary Examiner — Narayan K Bhat
(74) Attorney, Agent, or Firm — Oblon, McClelland, Maier & Neustadt, L.L.P.

(57) ABSTRACT

Disclosed are a reaction tube for nucleic acid amplification capable of controlling a liquid circulation path, a reaction apparatus for nucleic acid amplification comprising the
(Continued)

reaction tube, and a method for amplifying nucleic acid comprising a step of using the reaction tube. Also disclosed are a kit comprising the reaction tube, and use of the reaction tube in preparation of a kit.

19 Claims, 7 Drawing Sheets

Specification includes a Sequence Listing.

(51) Int. Cl.
    *B01L 3/00*     (2006.01)
    *B01L 7/00*     (2006.01)
    *C12Q 1/6844*     (2018.01)

(52) U.S. Cl.
    CPC ......... *B01L 3/502753* (2013.01); *B01L 7/525* (2013.01); *B01L 7/54* (2013.01); *C12M 1/24* (2013.01); *C12Q 1/6844* (2013.01); *B01L 2300/047* (2013.01); *B01L 2300/1805* (2013.01); *B01L 2400/0445* (2013.01)

(56) References Cited

U.S. PATENT DOCUMENTS

| | | | |
|---|---|---|---|
| 8,053,215 | B2 | 11/2011 | Hwang et al. |
| 8,187,813 | B2 | 5/2012 | Chen et al. |
| 2004/0152122 | A1 | 8/2004 | Hwang et al. |
| 2005/0074782 | A1 | 4/2005 | Krishnan et al. |
| 2006/0194207 | A1* | 8/2006 | Mitani .................. B01L 3/502 435/6.13 |
| 2010/0285536 | A1 | 11/2010 | Hwang et al. |
| 2012/0021463 | A1 | 1/2012 | Hwang et al. |
| 2013/0109021 | A1 | 5/2013 | Hwang |
| 2014/0065702 | A1* | 3/2014 | Tsai .......................... B01L 7/52 435/286.1 |
| 2014/0170707 | A1 | 6/2014 | Hwang et al. |

FOREIGN PATENT DOCUMENTS

| | | |
|---|---|---|
| CN | 101983236 A | 3/2011 |
| CN | 102803465 A | 11/2012 |
| CN | 103173434 A | 6/2013 |
| CN | 103421688 A | 12/2013 |

OTHER PUBLICATIONS

Bhuiya et al, Heat transfer performance for turbulent flow through a tube using double helical tape inserts, 2012, International Communications in Heat and Mass Transfer, 39, 818-825. (Year: 2012).*
Extended European Search Report dated Jan. 8, 2019 in Patent Application No. 16792183.2, citing documents AA and AW-AY therein, 8 pages.
Madhavi Krishnan et al., "PCR in a Rayleigh-Bénard Convection Cell" Science, vol. 298, XP055151409, Oct. 25, 2002, p. 793.
Hsiao-Fen Grace Chang, et al., "A Thermally Baffled Device for Highly Stabilized Convective PCR" Biotechnology Journal, vol. 7, No. 5, XP055526081, Feb. 7, 2012, pp. 662-666.
Wen Pin Chou, et al., "Rapid DNA Amplification in a Capillary Tube by Natural Convection with a Single Isothermal Heater" Biotechniques, vol. 50, No. 1, XP055170196, Jan. 1, 2011, pp. 52-57.
International Search Report dated Aug. 15, 2016 in PCT/CN2016/081649.

* cited by examiner

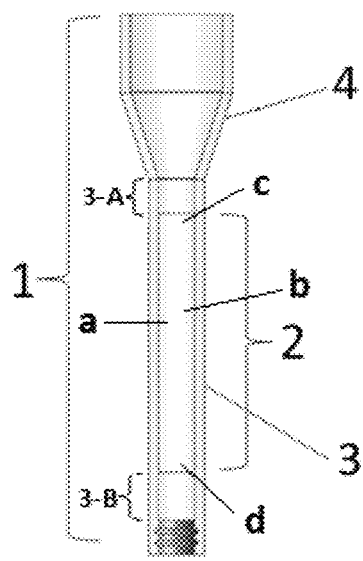
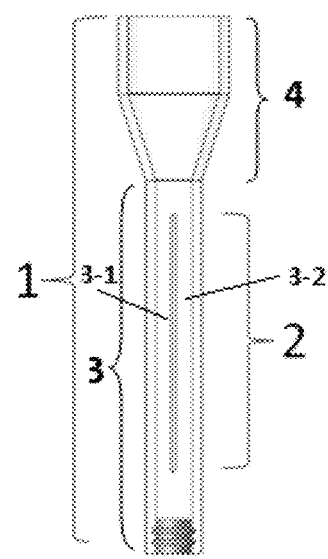
FIG. 2a
FIG. 2b
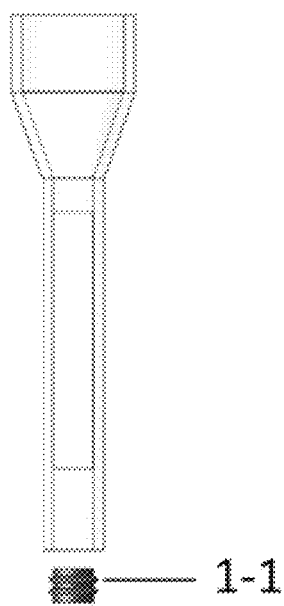
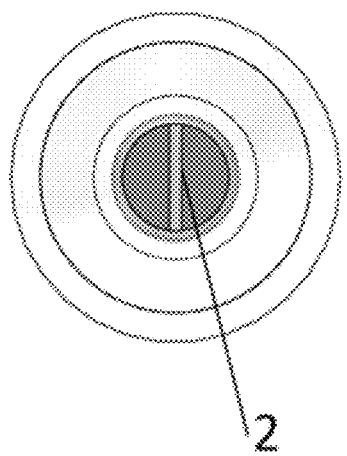
FIG. 2c
FIG. 2d

REACTION TUBE FOR NUCLEIC ACID AMPLIFICATION CAPABLE OF CONTROLLING LIQUID CIRCULATION PATH

TECHNICAL FIELD

The invention is in the field of molecular biology, particularly in the field of nucleic acid amplification. In particular, the invention relates to a reaction tube for nucleic acid amplification, and more particularly to a reaction tube for nucleic acid amplification capable of controlling a liquid circulation path. In addition, the invention also relates to a method for amplifying nucleic acid comprising using the reaction tube for nucleic acid amplification capable of controlling a liquid circulation path of the invention. In addition, the invention also relates to a reaction apparatus for nucleic acid amplification comprising the reaction tube. In addition, the invention also relates to a kit comprising the reaction tube, and use of the reaction tube in preparation of a kit.

TECHNICAL BACKGROUND

Polymerase chain reaction (PCR), is a technology for rapidly amplifying DNA in vitro, and each cycle includes three steps: denaturation, annealing and extension. Firstly, a sample of double-stranded DNA is heated at a high temperature of about 95° C., and hydrogen bonds between the double strands are broken so that DNA is separated into two complementary single-stranded DNA molecules, and this process is referred to as a high-temperature melting reaction; then, the temperature is rapidly lowered to about 50-65° C. at which the single-stranded DNA binds to a primer according to the principle of complementary base pairing, which is called a low-temperature annealing reaction; after the annealing reaction, the temperature is rapidly raised to about 72° C. to permit extension reaction, where single nucleotides are sequentially added from the 3'end of the primer by DNA polymerase at an appropriate concentration of magnesium ion to form a new DNA. After such process, one original double-stranded DNA molecule becomes two new DNA molecules, and the number of DNA molecules is doubled. After each cycle, the number of target nucleic acid molecules is doubled, and these newly formed double-stranded molecules can be used as templates for the next cycle. After 30 to 40 cycles, the number of target nucleic acid molecules can increase to nearly $10^9$ times. PCR is a method for obtaining a large number of target DNA segments in vitro, for further analysis and detection.

At present, the reaction devices for PCR mainly employ temperature-controlled metal blocks to heat PCR reaction tubes made of plastic, and by heating and cooling of the metal blocks to the equilibrium temperature, heat is transferred from the reaction tube to PCR reaction solution. The disadvantage of this device is that: the reaction volume is large, that is, the device usually has a large volume and heat capacity. Typically it takes 2-3 hours to complete a conventional PCR with 30 cycles, and most of the time is consumed by heating and cooling process, i.e., making the metal block to reach the equilibrium temperature and transferring heat from the reaction tube to the PCR reaction solution, therefore, fast and efficient PCR is difficult to be achieved.

In 2002, Madhavi Krishnan et al. reported a method named Rayleigh-Benard PCR (RB-PCR), based on the principle of heat conduction and thermal convection, using two constant temperature heat sources disposed at upper and lower regions respectively to establish a closed reaction cavity which has a temperature gradient from bottom to top, and thus convective motion of the PCR reagents occurs spontaneously, and makes the PCR reagents flow repeatedly through regions with different temperatures, to complete amplification. The amplification speed of this method is rapid, and the instrument is much simpler than traditional PCR instruments, but the amplification reagent should fill the entire closed cavity, resulting in difficulty in loading sample, and problems such as leakage and contamination.

Chou et al. in Taiwan University made improvements on the basis of the RB-PCR technology, by changing the closed reaction cavity to an open reaction tube with particular specification, and employing one single heat source of constant temperature to heat the bottom of the tube to drive the spontaneous circulation of reagents within the tube to complete amplification. This method solves the problem of leakage and contamination of RB-PCR.

However, common defects exist in the current amplification methods based on convective PCR, that is, flow path of the liquid in the tube is complicated. The flow path in the tube is a multilayer flow path nearly in the form of concentric ellipses (FIG. 1a). This complex multilayer flow path has the following problems in amplification:

1. Low Amplification Efficiency:

(a) Efficiency of denaturation: as shown in FIG. 1a, effective denaturation of templates or amplicons can occur when the templates or amplicons pass through region D1 where the temperature is not lower than the denaturation temperature required by the template or amplicon; while effective denaturation reaction cannot occur when the templates or amplicons pass through region D2 which is located higher than region D1, resulting in a low overall degeneration efficiency;

(b) Efficiency of annealing: As shown in FIG. 1a, effective annealing reaction may occur when the single-stranded templates and primers pass through region A1 where the temperature is not higher than the annealing temperature required by the templates and primers; while effective annealing reaction cannot occur when the single-stranded templates and primers pass through region A2 which is located lower than region A1, resulting in a low overall annealing efficiency 2. Poor Specificity of Amplification:

In the convection PCR, because of lack of an area and time period for annealing with a constant temperature, the temperature of the upper end of reaction tube is generally controlled to be lower than the annealing temperature of the primers by controlling the temperature field and flow field, to ensure a sufficient annealing of primers. However, when the single-stranded templates and (or) primers pass through a region where the temperature is too low in circulation, the specificity of annealing reaction is reduced, and non-specific pairing within one primer or between two primers, or between the primer and the template (or amplicon) may be formed easily, and as the extension reaction begins, non-specific amplification product is formed.

3. Differences Among the Parallel Amplification Reactions in Respective Tubes May Exist:

(a) As for qualitative detection at end-point of the reaction, the results mainly show the differences in amplification efficiency and product constitution: after denaturation, the non-specific amplification products as described in point 2 mentioned above will become the template in the next round of non-specific amplification, so that non-specific amplification is continuously enlarged, and will compete for primers, enzymes, dNTP and other reaction components availability with the correct amplification, resulting in inhibition of the correct amplification and reduction of the reaction efficiency. However, it is not known whether or when this non-specific reaction occurs, and the occurrence rate of this reaction is uncontrolled, that is, there is a certain randomness, which will cause inconsistency in term of the amplification efficiencies between reaction tubes wherein such non-specific amplification occurs. In the reaction tubes where the non-specific amplification occurs at an earlier time point or has a higher rate of occurrence, the reaction efficiency will be lower than that in the reaction tubes where the non-specific amplification occurs at a later time point or has a lower rate of occurrence. And in the two reaction tubes mentioned above, the reaction efficiencies are both lower than that in the reaction tubes where the non-specific amplification has not occurred. Similarly, there is a high proportion of non-specific products in the reaction tubes where the non-specific amplification occurs at an earlier time point or has a higher rate of occurrence, and there is a low proportion of non-specific products in the reaction tubes where the non-specific amplification occurs at an later time point or has a lower rate of occurrence, while in the reaction tubes where no non-specific amplification occurs, the products in tube are all correct amplification products.

(b) As for real-time quantitative detection, the results mainly show the differences in amplification efficiency per unit time: that is to say, real-time quantitative detection cannot be performed. As described above in points 1 and 2, when convective PCR reaction starts, it is not known if the double-stranded template can pass through the effective region for denaturation, or if single-stranded template and primer can pass through the effective region for annealing, and if non-specific reaction occurs during the annealing reaction. Therefore, at beginning of the reaction, differences in product constitution may be generated between different tubes. These differences not only may lead to problems described in the above 3(a), but also lead to differences in amount of products (templates) in different reaction tubes per unit time, and further result in differences in the time point when the exponential phase of amplification is entered, therefore, quantification of templates cannot be performed by traditional real-time monitoring method.

CONTENTS OF THE INVENTION

It is an object of the invention to provide a novel reaction tube for nucleic acid amplification and a method for nucleic acid amplification, to solve the problems in current convective PCR, such as low amplification efficiency, less specificity, great difference between reaction tubes and inaccurate quantification.

A first aspect of the invention provides a reaction tube for nucleic acid amplification comprising a tube body with one end closed, said tube body comprises a reservoir region and a nucleic acid amplification region located below the reservoir region, wherein an insert is disposed in said nucleic acid amplification region with an upper space remained above the insert and a lower space remained below the insert. When a reagent is injected into the reaction tube, the reagent is capable of moving along a circulation path through the upper space and the lower space in the reaction tube under an internal force or external force, due to a physical barrier effect of the insert.

Preferably, the insert is provided along the central axis of the tube body, and both sides of the insert are connected to the inner wall of the nucleic acid amplification region. The insert divides the nucleic acid amplification region into a first region and a second region along the central axis of the tube body, and the first region and the second region are connected via an upper region and a lower region of the nucleic acid amplification region.

Preferably, the distance between the lower end of the insert and the bottom of the tube body is greater than 0 mm (e.g., greater than or equal to 1 mm) and less than ½ of the height of the nucleic acid amplification region. More preferably, the distance between the lower end of the insert and the bottom of the tube body (e.g., greater than or equal to 1 mm) and less than ⅓ of the height of the nucleic acid amplification region. Further preferably, the distance between the lower end of the insert and the bottom of the tube body is greater than 0 mm (e.g., greater than or equal to 1 mm) and less than or equal to 4 mm.

Preferably, the distance between the upper end of the insert and the top of the nucleic acid amplification region is greater than 0 mm (e.g., greater than or equal to 1 mm) and less than ½ of the height of the nucleic acid amplification region. More preferably, the distance between the upper end of the insert and the top of the nucleic acid amplification region is greater than 0 mm (e.g., greater than or equal to 1 mm) and less than ⅓ of the height of the nucleic acid amplification zone. Further preferably, the distance between the upper end of the insert and the top of the nucleic acid amplification region is greater than 0 mm (e.g., greater than or equal to 1 mm) and less than or equal to 3 mm.

Preferably, the bottom of the tube body is closed by means of a bottom plug which cooperates with the tube body. Preferably, the tube body and the bottom plug are hermetically connected to each other by a rotatable threaded structure, or a ring-like bayonet structure, or a bump latch structure, or by other hermetic connection as known in the art.

Preferably, the tube body further comprises a tube cover cooperating therewith. Preferably, the tube body and the tube cover are hermetically connected to each other by a rotatable threaded structure, or a ring-like bayonet structure, or a bump latch structure, or by other hermetic connection as known in the art.

Preferably, the nucleic acid amplification region has a height/inner diameter ratio of 3 to 12. More preferably, the nucleic acid amplification region has a height/inner diameter ratio of 6 to 9.

Preferably, the nucleic acid amplification region has a volume of 30 to 200 µl. More preferably, the nucleic acid amplification region has a volume of 40 to 150 µl.

Preferably, the tube body and insert are made of a heat-resistant material. For example, the heat-resistant material is selected from, glass, polycarbonate, polypropylene, polyethersulfone and polysulfone.

In addition, it is preferred that the inner wall of the tube body can be passivated by bovine serum albumin (BSA) or a silylating agent, etc., thereby reducing an adsorption of nucleic acid and certain components in the reagent.

In a preferred embodiment, the inner cavity of the nucleic acid amplification region has a columnar hollow structure having equal upper and lower inner diameters, or has a tapered hollow structure or a multi-layered trapezoidal hollow structure, having a cross section with wide top and narrow bottom. Amplification of nucleic acid, RNA transcription, and acquisition of signal in real-time detection are all performed in this region.

In another preferred embodiment, the nucleic acid amplification region may be provided with a visible volume scale marking.

Another aspect of the invention provides a reaction apparatus for nucleic acid amplification comprising the reaction tube according to any one of the first aspect of the invention and one or more temperature controllers capable of providing or removing heat, said temperature controller is arranged outside or inside the reaction tube.

Yet another aspect of the present invention provides a kit comprising the reaction tube according to any one of the first aspect of the invention.

Yet another aspect of the invention provides a method for amplifying a target nucleic acid in a sample, comprising using the reaction tube according to any one of the first aspect of the invention or the reaction apparatus for nucleic acid amplification according to any one of the invention.

Preferably, the nucleic acid is DNA or RNA.

Preferably, the amplification is PCR reaction or reverse transcription reaction.

Preferably, the method comprises the steps of:

1) injecting a reagent for nucleic acid amplification reaction into the reaction tube according to any one of the first aspect of the invention;

2) filling the reagent into the nucleic acid amplification region by vibrating, centrifuging or other ways; optionally, covering the surface of the reagent with a nonvolatile substance (e.g., paraffin oil or a low melting point wax) or closing the reaction tube with a tube cover;

3) providing or removing heat at a specific site of the reaction tube by a temperature controller to complete RNA reverse transcription and/or DNA amplification reaction;

4) optionally, detecting the amplified product during or after nucleic acid amplification.

The invention also provides use of the reaction tube according to any one of the first aspect of the invention or the reaction apparatus for nucleic acid amplification according to any one of the invention in nucleic acid amplification.

The invention also provides use of the reaction tube according to any one of the first aspect of the invention in preparation of a kit, and the kit is used for nucleic acid amplification.

BENEFICIAL EFFECT OF THE INVENTION

In the invention, due to a physical barrier effect of the insert the reagent in the tube can only pass under and over the insert in the movement driven by an external force or internal force; and through one or more temperature controllers arranged outside or inside the reaction tube, a specific region in the reaction tube can be heated. By this way, denaturation reaction may occur when the reagent in circulation passes through a certain region below the insert, and annealing reaction may occur when the reagent in circulation passes through a region above the insert. Such circulation path and the temperature control mode can achieve the following benefits:

1. Improving amplification efficiency: (a) improving denaturation efficiency: as shown in FIG. 1b, due to the physical barrier effect of insert 2, when the reagent in circulation moves to the lower end of the reaction tube, it can only pass through the region D1 below insert 2, and by means of the temperature controller, the region can be maintained at a temperature higher than the temperature required for denaturation reaction. Therefore, effective denaturation reaction may occur when the reagent in circulation passes through the region D1 below the insert 2 of the reaction tube; (b) improving annealing efficiency: as shown in FIG. 1b, due to the physical barrier effect of the insert 2, when the reagent in circulation moves to the upper end of the reaction tube, it can only pass through the region A1 above the insert 2, and by means of the temperature controller, the region can be maintained at a desired temperature for annealing of a specific primer. Therefore, effective annealing reaction may occur when the reagent in circulation passes over the insert 2 of the reaction tube.

2. Ensuring specificity of amplification: as shown in FIG. 1b, due to the physical barrier effect of the insert 2, when the reagent in circulation moves to the upper end of the reaction tube, it can only pass through the region A1 above the insert 2, and by means of the temperature controller, the region can be maintained at a desired temperature for annealing of a specific primer without being far below the annealing temperature of the specific primer. Thus, when the reagent in circulation passes through the region, non-specific pairing within one primer or between two primers, or between the primer and the template (or amplicon) cannot occur, resulting in no non-specific amplification.

3. Improving consistency among the amplifications in different tubes:

(a) Improving consistency between amplifications in different tubes by increasing the specificity: as described in point 2 mentioned above, since the random formation of non-specific product which will compete for primers, enzymes, dNTP and other reaction components with correct amplification will not occur, the efficiency of correct amplification would not be affected by non-specific amplification, and thus the consistency among amplifications in different tubes per unit time can be improved; (b) Improving consistency among amplifications in different tubes by increasing the amplification efficiency: when convective PCR begins, due to the physical barrier effect of the insert 2 in the reaction tube and the control function by the temperature controller, all the double-stranded templates in the tube can pass through the region for effective denaturation and undergo a denaturation reaction; and when the reagent in circulation moves to the upper end of the reaction tube, all the single-stranded templates and primers can pass through the region for annealing and undergo an annealing reaction. Therefore, invalid cycle due to tandem circulation path (i.e., when the reagent in circulation moves to the lower position, it does not pass through the region at a desired temperature for denaturation, and (/or) when the reagent in circulation moves to the upper position, it does not pass through the region at a desired temperature for annealing) will not occur, so as to improve consistency among amplifications in different tubes per unit time. (c) due to the improved consistency between amplifications, the consistency of the amplified products at the end point among parallel reactions can be improved, and thus the consistency among amplifications per unit time in parallel reactions can also be improved. Therefore, quantitation of the initial templates in convective PCR amplification can be realized by real time fluorescence detection.

The embodiments of the invention will be described in detail with reference to the accompanying drawings and examples. However, it will be understood by those skilled in the art that the following drawings and examples are intended to be illustrative of the invention only and are not intended to limit the scope of the invention. Various objects and advantageous aspects of the invention are apparent to those skilled in the art, according to the following detailed description of the drawings and preferred embodiments.

BRIEF DESCRIPTION OF THE DRAWINGS

FIG. 2a is a front view of a reaction tube capable of controlling a spontaneous circulation path of liquid;

FIG. 2b is a side view of the reaction tube capable of controlling a spontaneous circulation path of liquid;

FIG. 2c is a front exploded view of the reaction tube capable of controlling a spontaneous circulation path of liquid;

FIG. 2d is a top view of the reaction tube capable of controlling a spontaneous circulation path of liquid;

SPECIFIC MODES FOR CARRYING OUT THE INVENTION

In the invention, the scientific and technical terms used herein have the same meaning as commonly understood by those skilled in the art, unless otherwise specified. Also, the laboratory procedures of molecular genetics, nucleic acid chemistry, and immunological used herein are the routine procedures that are widely used in the corresponding fields. Meanwhile, for the purpose of better understanding the invention, definitions and explanations of related terms are provided below.

As used herein, the term "amplification" should be understood in a broad sense, comprising any process of preparing DNA from RNA or DNA, which includes but is not limited to PCR reaction, reverse transcription reaction and various variations thereof (e.g., real-time PCR reaction).

As used herein, the term "nucleic acid" includes ribonucleic acid (RNA) and deoxyribonucleic acid (DNA).

Figures 1A, 1B:
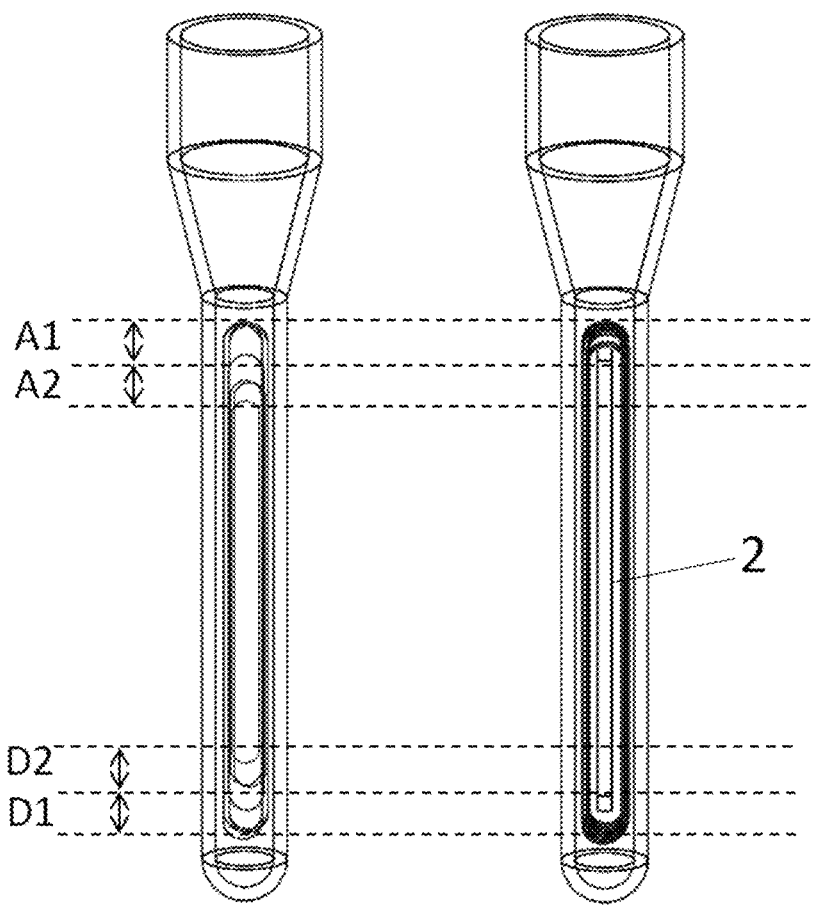
FIG. 1a shows a circulation trajectory in a natural convection state.
FIG. 1b shows a circulation trajectory of liquid controlled by the reaction tube of the invention.

FIG. 1a shows a motion trajectory of the circulation in the reaction tube in a natural convection state. Convection can occur if a temperature difference is developed in specific section within the reaction tube. Therefore, in space of the reaction tube, circulation trajectory is not single, but presents a multi-layer and multi-directional feature. Then, in this multi-layer circulation, (1) templates or amplicons can undergo effective denaturation reaction when passing through region D1 where the temperature is not lower than the temperature required for denaturation; while templates or amplicons cannot undergo effective denaturation reaction when passing through region D2 located above region D1, resulting in a low overall denaturation efficiency; (2) single-stranded templates and primers can undergo effective annealing reaction when passing through region A1 where the temperature is not higher than the temperature required for annealing; while single-stranded templates and amplicons cannot undergo effective annealing reaction when passing through region A2 located below region A1, resulting in a low overall annealing efficiency; (3) When single-stranded templates and (or) primers pass through a region where the temperature is overly low in the circulation, specificity of annealing is reduced, and non-specific pairing within one primer or between two primers, or between the primer and the template (or amplicon) may be formed easily, and as the extension reaction begins, non-specific amplification product is formed; (4) After the denaturation, the non-specific amplified product becomes the template for next round of non-specific amplification, so that the non-specific amplification is enlarged continuously, and competes for primers, enzymes, dNTP and other reaction components availability with correct amplification, resulting in inhibition of correct amplification and reduction of reaction efficiency. However, it is not known whether or when this non-specific reaction occurs, and the occurrence rate of this reaction is uncontrolled, that is, there is a certain randomness, which will lead to inconsistency of amplification efficiencies among reaction tubes where such non-specific amplification occurs; (5) Said inconsistency of amplification will appear as a difference in the effective amplification efficiency per unit time in real-time quantitative detection, which leads to the inability to quantify the nucleic acid templates by using the traditional fluorescence quantitative PCR method with a standard curve.

FIG. 1b shows a circulation path, which is a unidirectional, relatively concentrated and regular circulation trajectory formed on the basis of natural convection and under control of a physical barrier. In the reaction tube capable of controlling a liquid circulation path, due to the physical barrier effect of insert 2 within the reaction tube, when the reagent in circulation moves to the lower region of the reaction tube, it can only pass through the space below the insert 2. And by means of the temperature controller, said region can be maintained at a temperature higher than the temperature required by the denaturation reaction. Therefore, when the reagent in circulation passes under the insert 2 of the reaction tube, effective denaturation reaction may occur. Also, due to the physical barrier effect of insert 2 in the reaction tube, when the reagent in circulation moves to the upper region of the reaction tube, it can only pass through the space above the insert 2, and by means of the temperature controller, said region can be maintained at a temperature required by annealing of specific primers. Therefore, when the reagent in circulation passes over the insert 2 in the reaction tube, effective annealing reaction may occur.

Referring to FIGS. 2a, 2b, 2c, and 2d, for the practice of the method described above, the invention firstly provides a preferred embodiment of a practicable reaction tube for nucleic acid amplification capable of controlling a liquid circulation path, comprising a tube body 1 with one end closed, said tube body 1 comprises a reservoir region 4 and a nucleic acid amplification region 3 located below the reservoir region; an insert 2 is disposed in said nucleic acid amplification region 3 with an upper space remained above the insert and a lower space remained below the insert. When a reagent is injected into the reaction tube, the reagent is capable of moving along a circulation path through the upper space and the lower space in the reaction tube under an internal force or external force, due to a physical barrier effect of the insert.

Preferably, the insert 2 is provided along the central axis of the tube body 1, and both sides a and b of the insert are connected to the inner wall of the nucleic acid amplification region. Further preferably, the sides a and b of the insert are hermetically connected to the inner wall of the nucleic acid amplification region 3. The insert 2 divides the nucleic acid amplification region 3 into a first region 3-1 and a second region 3-2 along the central axis of the tube body 1, and the first region 3-1 and the second region 3-2 are connected via an upper region 3-A and a lower region 3-B of the nucleic acid amplification region 3.

Preferably, the distance between the lower end d of the insert 2 and the bottom of the tube body 1 (i.e., the height of the lower region 3-B of the nucleic acid amplification region 3) is greater than 0 mm (e.g., greater than or equal to 1 mm) and less than ½ of the height of the nucleic acid amplification region 3. More preferably, the distance between the lower end d of the insert 2 and the bottom of the tube body 1 is greater than 0 mm (e.g., greater than or equal to 1 mm) and less than ⅓ of the height of the nucleic acid amplification region 3. Further preferably, the distance between the lower end d of the insert 2 and the bottom of the tube body 1 is greater than 0 mm (e.g., greater than or equal to 1 mm) and less than or equal to 4 mm.

Preferably, the distance between the upper end c of the insert 2 and the top of the nucleic acid amplification region 3 (i.e., the height of the upper region 3-A of the nucleic acid amplification region 3) is greater than 0 mm (e.g., greater than or equal to 1 mm) and is less than ½ of the height of the nucleic acid amplification region 3. More preferably, the distance between the upper end c of the insert 2 and the top of the nucleic acid amplification region 3 is greater than 0 mm (e.g., greater than or equal to 1 mm) and less than ⅓ of the height of the nucleic acid amplification region 3. Further preferably, the distance between the upper end c of the insert 2 and the top of the nucleic acid amplification region 3 is greater than 0 mm (e.g., greater than or equal to 1 mm) and less than or equal to 3 mm.

Preferably, the bottom of the tube body 1 is closed by means of a bottom plug 1-1 which cooperates with the tube body 1. For example, the tube body and the bottom plug are hermetically connected to each other by a rotatable threaded structure, or a ring-like bayonet structure, or a bump latch structure, or by other hermetic connection as known in the art.

Preferably, the tube body 1 further comprises a tube cover cooperating therewith. The tube body 1 and the tube cover are connected to each other by a rotatable threaded structure, or a ring-like bayonet structure, or a bump latch structure, or by other hermetic connection as known in the art.

Preferably, the nucleic acid amplification region 3 has a height/inner diameter ratio of 3 to 12. More preferably, the nucleic acid amplification region 3 has a height/diameter of 6 to 9, for example, 7 to 8. It is further preferable that the nucleic acid amplification region 3 has an inner diameter of W mm or less, for example 5 mm or less, and also has an inner diameter less than the inner diameter of the reservoir region 4. A structure with said dimension and ratio of the invention, can efficiently ensure and promote the spontaneous formation of a continuous and stable convection of the liquid in the reaction tube. In the invention, the region having a larger inner diameter in the upper portion of the tube body 1 can be served as the reservoir region 4. Since the inner diameter of the nucleic acid amplification region 3 is relatively small, a pipette tip cannot be easily inserted into the bottom, and the liquid also cannot flow to the bottom spontaneously. Thus, the reaction reagent may be temporarily stored in the reservoir region 4 and then the reaction reagent in the reservoir region 4 can be introduced into the nucleic acid amplification region 3 by centrifugation, vibration or other methods, where the amplification reaction or the acquisition of fluorescence signal is completed. Moreover, the reservoir region 4 has a larger diameter relative to the nucleic acid amplification region 3, and thus it is easier to grasp and hold the tube, providing a great convenience for an operator in preparation of liquid.

Preferably, the nucleic acid amplification region 3 has a volume of 30 to 200 μl. More preferably, the nucleic acid amplification region 3 has a volume of 40 to 150 μl.

Further, the inner cavity of the nucleic acid amplification region 3 can has a tapered hollow structure or a multi-layered trapezoidal hollow structure, having a cross section with wide top and narrow bottom, and amplification of nucleic acid, RNA transcription, acquisition of signal in real-time detection are all performed in this region. The advantages of the inner cavity with wide top and narrow bottom of the nucleic acid amplification region 3 are the following: when the convention of reagent occurs due to a temperature gradient from top to bottom within the reaction tube, the reagent can has a lengthened path in the region with wider inner diameter in the upper portion of the reaction tube, that is, the time period of "extension" step in PCR reaction can be increased, which can facilitate extension of a long fragment. Of course, for ease of manufacture, the inner cavity of the nucleic acid amplification region 3 may also be a columnar hollow structure having equal upper and lower inner diameters.

Preferably, the tube body 1 and the insert 2 are made of a heat-resistant material. For example, the heat-resistant material is selected from, glass, polycarbonate (PC), polypropylene (PE), polyethersulfone (PES) and polysulfone (PSF).

In addition, it is preferable that the inner wall of the tube body 1 can be passivated by bovine serum albumin (BSA), a silylating agent or the like, thereby reducing an adsorption of nucleic acid or certain components in the reaction reagent.

The above-mentioned reaction tube may contain: a sample of nucleic acid to be tested, DNA polymerase, deoxyadenosine triphosphate, deoxycytidine triphosphate, deoxyguanosine triphosphate, deoxythymidine triphosphate, reaction buffer, divalent magnesium ion, PCR additives as non-main components (e.g., betaine, bovine serum albumin, DMSO, etc.) and at least two oligonucleotide primers that are specifically complementary to the nucleic acid sequence to be tested, and optionally, fluorescent dye or specific fluorescent probe capable of binding double-stranded DNA. Thereafter, to prevent evaporation, a nonvolatile substance having a low density (such as paraffin oil or various low melting point waxes) is used to cover the surface of reagent, or a tube cover is used to close the reaction tube.

Meanwhile, the invention also provides a reaction apparatus for nucleic acid amplification comprising a reaction tube according to any one of the invention and one or more temperature controllers capable of providing or removing heat, said temperature controller is provided inside or outside the reaction tube. The temperature controller has the following functions: (1) establishing a temperature gradient and a density gradient for the reagent in the reaction tube based on the Rayleigh-Benard principle, so as to drive the spontaneous circulation of the reaction reagent in the reaction tube; (2) controlling the temperature of the reaction tube and of the reagent at a specific site in the tube; (3) completing polymerase chain reaction and other nucleic acid amplification reactions, through the spontaneous circulation and temperature control of the reagent. A temperature controller capable of establishing a temperature gradient and a density gradient of a reagent in a reaction tube is well known in the art and can be found, for example, in the invention patents CN103173434A, CN1571849A and CN101983236A.

Figure 3:
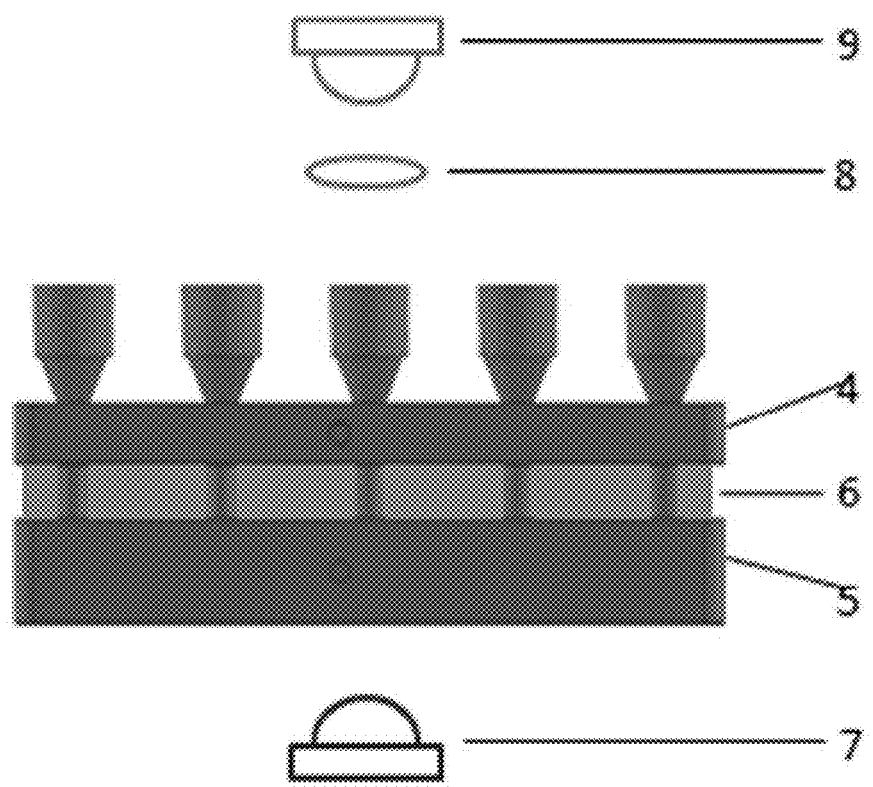
FIG. 3 shows a diagram illustrating a device for heating and fluorescence detection of a reaction tube capable of controlling a spontaneous circulation path of liquid.

A preferred embodiment of the temperature controller of the invention is shown in FIG. 3, preferably, the temperature controller comprises an upper heating module 4 and a lower heating module 5 for providing or removing heat in the bottom and upper portions of the reaction tube, respectively, and by such temperature control, suitable temperature for denaturation is provided at the bottom of the reaction tube capable of controlling a liquid circulation path to realize effective PCR amplification, so as to ensure the reagent flowing under the insert can undergo effective denaturation reaction; and suitable temperature for annealing is also provided at the upper portion of the reaction tube to ensure that the reagent flowing over the insert can undergo effective annealing reaction. In addition, a module 6 with a lower heat transfer coefficient is disposed between the upper and lower heating modules to wrap the non-direct heating region of the reaction tube. As such, this can avoid interference caused by exposure of the region to external air, and can also avoid the differences in the distribution of temperature field between different reaction tubes caused by difference in heat-radiating ability between central position and edge position of a multi-channel module.

Preferably, the apparatus further comprises a module for real-time detection of fluorescence signal. The module comprises an excitation light source 7, a filter 8 and a photodetector 9, and can perform a fast equilibrium scanning of a plurality of specimen in a time on the order of milliseconds.

The invention is not limited to the reaction tube and the detection device described in FIGS. 2 and 3, and changes in the heating mode and the shape of the reaction tube are all within the scope of the invention.

Figure 4:
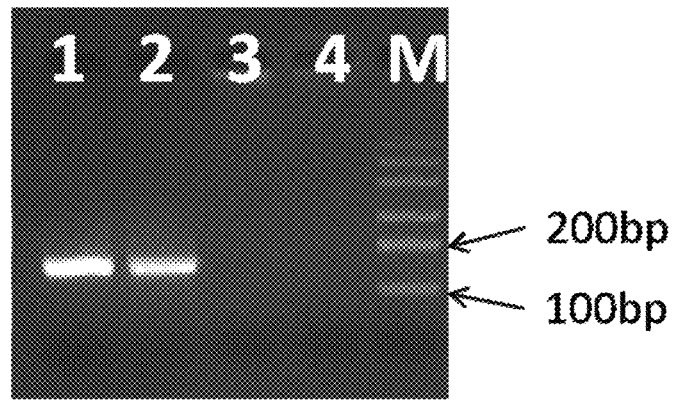
FIG. 4 shows the results of agarose gel electrophoresis of the amplified products obtained from DNA templates by using the reaction tube of the invention.

FIG. 4 shows the results of agarose gel electrophoresis of the amplified products obtained from a DNA template by using the reaction tube for nucleic acid amplification capable of controlling a spontaneous circulation path of liquid according to the invention. In the application, the reaction tube contains: DNA template to be tested, DNA polymerase, deoxyadenosine triphosphate, deoxycytidine triphosphate, deoxyguanosine triphosphate, deoxythymidine triphosphate, reaction buffer, divalent magnesium ion, PCR additives as non-main components (e.g., betaine, bovine serum albumin, DMSO, etc.) and at least two oligonucleotide primers that are specifically complementary to the nucleic acid sequence to be tested. Thereafter, to prevent evaporation, a nonvolatile substance having a low density (such as paraffin oil or various low melting point waxes) is used to cover the surface of the reagent, or a tube cover is used to close the reaction tube. During amplification, the reaction tube is placed in a heating device, and the heating module located outside the bottom of the reaction tube is set to 95° C., the heating module located outside the upper portion of the reaction tube is set to 60° C., and the reaction time is set to 30 minutes. The reagent in the reaction tube will flow continuously under the drive of the temperature difference and only pass over and under the insert due to the physical barrier effect of the insert in the reaction tube. And the reagent can undergo denaturation reaction when flowing under the insert, and undergo annealing reaction when flowing over the insert, and then undergo extension reaction at a temperature range for polymerase activity. After amplification, 5 μl of the product is taken from the tube and subjected to agarose gel electrophoresis. Lane 1 and lane 2 show results of amplification of positive samples, and lane 3 and lane 4 show results of amplification of negative control (DEPC water). As can be seen from the results, the reaction tube of the invention enables the amplification of DNA templates.

Figure 5:
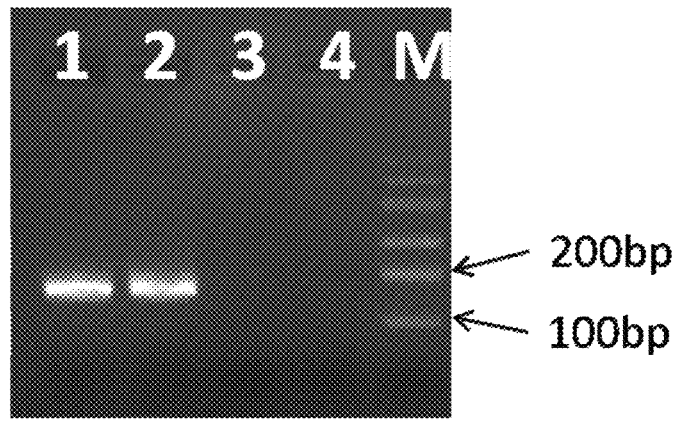
FIG. 5 shows the results of agarose gel electrophoresis of the amplified products obtained from RNA templates by using the reaction tube of the invention.

FIG. 5 shows the results of agarose gel electrophoresis of the amplified products obtained from a RNA template by using the reaction tube for nucleic acid amplification capable of controlling a spontaneous circulation path of liquid according to the invention. Unlike DNA amplification, the reaction tube also contains reverse transcriptase for synthesis of cDNA from RNA templates, in addition to the above-mentioned agents required for the DNA amplification. Moreover, the temperature settings of the heating modules for RNA amplification are also different: the temperature of the heating module located outside the bottom of the reaction tube is first set to 60° C., maintained for 20 minutes and then raised to 95° C. for 30 minutes; the temperature of the heating module located outside the upper part of the reaction tube is set to a constant temperature of 60° C. for 50 minutes. Similarly, after amplification, 5 μl of the product is taken from the tube and subjected to agarose gel electrophoresis. Lane 1 and lane 2 are the results of positive samples, and lane 3 and lane 4 are the results of negative control (DEPC water). As can be seen from the electropherogram, the reaction tube of the invention also enables amplification of RNA templates.

Figure 6A:
FIG. 6a shows the results of agarose gel electrophoresis of the amplified products obtained by using the reaction tube capable of controlling a spontaneous circulation path of liquid.
Figure 6B:
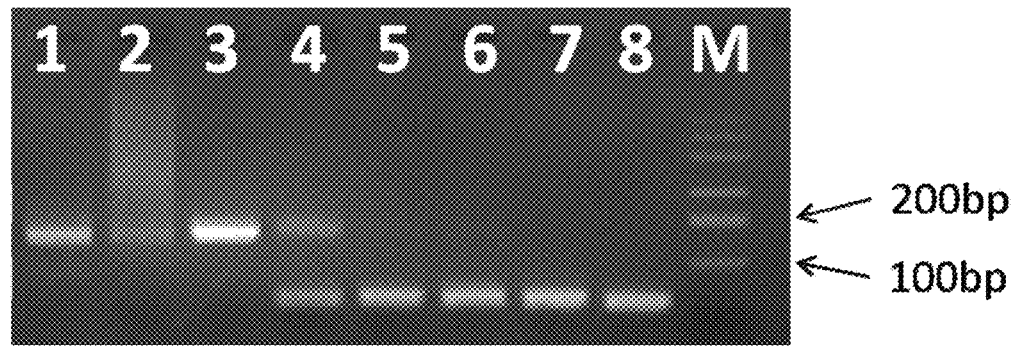
FIG. 6b shows the results of agarose gel electrophoresis of the amplified products obtained by using the reaction tube without the function of circulation control.

FIG. 6 illustrates that consistency and specificity of amplification between tubes can be improved by using the reaction tube for nucleic acid amplification capable of controlling a spontaneous circulation path of liquid according to the invention, as compared with the previous convective PCR method. Amplification is carried out on four identical template samples extracted from cytomegalovirus (CMV)-positive samples (CMV DNA concentration is $10^3$ copies/tube), and four identical template samples extracted from CMV-negative and HBV-positive samples (HBV DNA concentration is $10^6$ copies/tube), by using the reaction tubes capable of controlling a spontaneous circulation path of liquid according to the invention or the reaction tubes without the function of circulation control with the same heating device, respectively. The results of the amplification in the reaction tube capable of controlling a spontaneous circulation path of liquid according to the invention are shown in FIG. 6a, and the results of the amplification in the reaction tube without the function of circulating control are shown in FIG. 6b. Lanes 1-4 show the amplification results of the 4 identical samples positive for CMV nucleic acid, and lanes 5-8 are the amplification results of the samples negative for CMV nucleic acid and positive for HBV nucleic acid as control. The results show that the consistency between the results detected at end point of the 4 positive samples amplified in the reaction tubes of the invention in parallel (FIG. 6a, lanes 1-4), is significantly superior to the consistency between the results of the samples amplified in the reaction tubes without the function of circulation control (FIG. 6b, lanes 1-4), indicating that the consistency of amplification among tubes can be improved by using the reaction tube capable of controlling a spontaneous circulation path of liquid according to the invention. In addition, the results detected at end point also show a significant reduction of non-specific amplification in the 4 negative samples amplified in the reaction tubes of the invention in parallel (FIG. 6a, lanes 5-8), compared with the samples amplified in the reaction tubes without the function of circulation control (FIG. 6b, lanes 5-8), indicating that the reaction tube capable of controlling a spontaneous circulation path of liquid according to the invention can improve the specificity of the amplification.

Figure 7A:
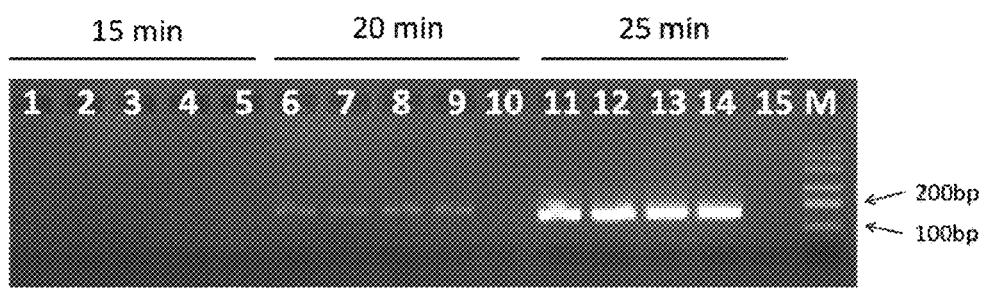
FIG. 7a shows the results of agarose gel electrophoresis of the amplified products obtained by using the reaction tube capable of controlling a spontaneous circulation path of liquid for different amplification times.
Figure 7B:
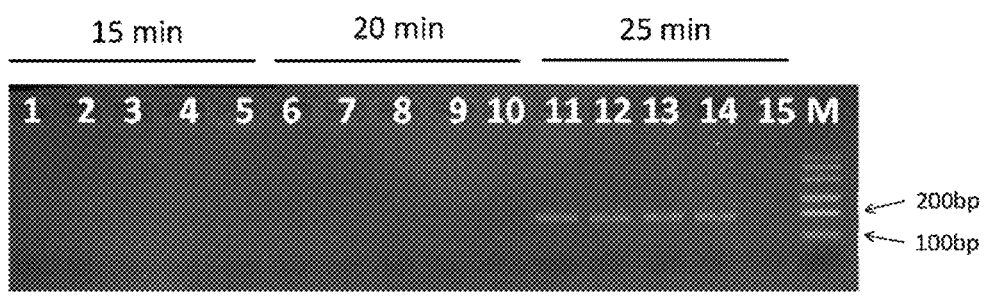
FIG. 7b shows the results of agarose gel electrophoresis of the amplified products obtained by using the reaction tube without the function of circulation control for different amplification times.

FIG. 7 illustrates that amplification rate can be improved by using the reaction tube capable of controlling a spontaneous circulation path of liquid according to the invention as compared with the previous convective PCR method. Amplification is carried out on 3 groups for 15 minutes, 20 minutes and 25 minutes, respectively. For each group, 4 identical samples of CMV DNA having a concentration of $10^3$ copies/ml, and a sample of DEPC water as negative control, are amplified in parallel, by using the reaction tubes capable of controlling a spontaneous circulation path of liquid according to the invention or the reaction tubes without the function of circulation control with the same heating device, respectively. The amplification results obtained by the reaction tube capable of controlling a spontaneous circulation path of liquid according to the invention are shown in FIG. 7a, and amplification results obtained by the reaction tube without the function of circulation control are shown in FIG. 7b. The results show that, when amplification is performed with the reaction tube of the invention, after 20 minutes of amplification, a weak band can be observed in positive samples, and after 25 minutes, a strong band can be observed in positive samples; while when amplification is performed with the reaction tube without the function of circulation control, a weak band can be observed in positive samples until 25 minutes after start of amplification reaction. This demonstrates that the amplification efficiency can be improved by the reaction tube for nucleic acid amplification capable of controlling a spontaneous circulation path of liquid according to the invention as compared with the previous convective PCR method.

FIG. 8 illustrates that accuracy of quantitative detection can be improved by the reaction tube capable of controlling a spontaneous circulation path of liquid according to the invention as compared with the previous convective PCR method. Amplification is carried out on a positive sample of human cytomegalovirus (CMV) DNA having a concentration of $10^6$ copies/tube, a positive sample of CMV DNA having a concentration of $10^5$ copies/tube, and a negative sample of DEPC water, by using the reaction tubes capable of controlling a spontaneous circulation path of liquid according to the invention or the reaction tubes without the function of circulation control with the same heating device, respectively. And real time detection of amplification is performed with taqman hydrolysis probe. The results show that, the repeatability of the results from samples with same concentration obtained by the reaction tubes of the invention is obviously higher than that obtained by the reaction tubes without the function of circulation control.

EXAMPLES

The invention is now described with reference to the following examples (which are used only for the purpose of illustration and are not intended to limit the invention).

Unless otherwise specified, the molecular biology experimental methods and immunoassays used in the invention are carried out substantially in accordance with the methods as described in J. Sambrook et al., Molecular Cloning: Laboratory Manual, 2nd Edition, Cold Spring Harbor Laboratory Press, 1989, and F. M. Ausubel et al., Current Protocols in Molecular Biology, 3rd edition, John Wiley & Sons, Inc., 1995; enzymes are used under the conditions recommended by manufacturers of the products. It will be understood by those skilled in the art that the examples are used for illustrating the invention, but not intended to limit the scope of the invention as claimed.

Example 1: A Reaction Tube that Controls a Spontaneous Circulation Path of Liquid As shown in FIGS. 2a, 2b, 2c and 2d, the reaction tube for nucleic acid amplification of the invention capable of controlling a circulation path of liquid comprises a tube body 1 with one end closed, the tube body 1 comprises a reservoir region 4 and a nucleic acid amplification region 3 provided below the reservoir region, and an insert 2 is disposed in the nucleic acid amplification region 3 with an upper space remained above the insert and a lower space remained below the insert 2. When a reagent is injected into the reaction tube, the reagent is capable of moving along a circulation path through the upper space and the lower space in the reaction tube under an internal force or external force, due to a physical barrier effect of the insert 2.

Preferably, the insert 2 is provided along the central axis of the tube body 1, and both sides a and b of the insert are connected to the inner wall of the nucleic acid amplification region 3. The insert 2 divides the nucleic acid amplification region 3 into a first region 3-1 and a second region 3-2 along the central axis of the tube body 1, and the first region 3-1 and the second region 3-2 are connected via an upper region 3-A and a lower region 3-B of the nucleic acid amplification region 3.

Preferably, the distance between the lower end d of the insert 2 and the bottom of the tube body 1 (i.e., the height of the lower portion 3-B of the nucleic acid amplification region 3) is greater than 0 mm (e.g., greater than or equal to 1 mm) and less than ½ of the height of the nucleic acid amplification region 3, for example, less than ⅓ of the height of the nucleic acid amplification region, for example, less than or equal to 4 mm.

Preferably, the distance between the upper end c of the insert 2 and the top of the nucleic acid amplification region 3 (i.e., the height of the upper region 3-A of the nucleic acid amplification region 3) is greater than 0 mm (e.g., greater than or equal to 1 mm) and less than ½ of the height of the nucleic acid amplification region 3, for example, less than ⅓ of the height of the nucleic acid amplification region, for example, less than or equal to 3 mm.

Preferably, the bottom of the tube body 1 is closed by means of a bottom plug 1-1 which cooperates with the tube body 1. Preferably, the tube body and the bottom plug are hermetically connected to each other by a rotatable threaded structure, or a ring-like bayonet structure, or a bump latch structure, or by other hermetic connection as known in the art.

Preferably, the nucleic acid amplification region 3 has a height/inner diameter ratio of 3 to 12. And more preferably, the nucleic acid amplification region 3 has a height/inner diameter ratio of 6 to 9.

Preferably, the nucleic acid amplification region 3 has a volume of 30 to 200 µl. And more preferably, the nucleic acid amplification region 3 has a volume of 40 to 150 µl.

Preferably, the inner cavity of the nucleic acid amplification region 3 may be a tapered hollow structure or a multi-layered trapezoidal hollow structure, having a cross section with wide top and narrow bottom, or a columnar hollow structure having equal upper and lower inner diameters. Amplification of nucleic acid, RNA transcription, acquisition of signal in real-time detection are all performed in this region.

The tube body 1 and the insert 2 are made of a heat-resistant material. For example, the heat-resistant material is selected from, glass, polycarbonate (PC), polypropylene (PE), polyethersulfone (PES) and polysulfone (PSF).

In addition, it is preferred that the inner wall of the tube body 1 can be passivated by bovine serum albumin (BSA), a silylating agent, etc., thereby reducing an adsorption of nucleic acid or certain components in the reaction reagent.

The above-mentioned reaction tube may contain: a sample of nucleic acid to be tested, DNA polymerase, deoxyadenosine triphosphate, deoxycytidine triphosphate, deoxyguanosine triphosphate, deoxythymidine triphosphate, reaction buffer, divalent magnesium ion, PCR additives as non-main components (e.g., betaine, bovine serum albumin, DMSO, etc.) and at least two oligonucleotide primers that are specifically complementary to the nucleic acid sequence to be tested, and optionally, fluorescent dye or specific fluorescent probe capable of binding double-stranded DNA. Thereafter, to prevent evaporation, a nonvolatile substance having a low density (such as paraffin oil or various low melting point waxes) is used to cover the surface of reagent, or a tube cover is used to close the reaction tube.

Example 2: Amplification and Detection of DNA Templates in the Reaction Tube for Nucleic Acid Amplification Capable of Controlling a Liquid Circulation Path of Example 1

1. Experimental Materials

Chemical reagents: SpeedSTAR HS DNA polymerase (TaKaRa), 10× Fast Buffer I ($Mg^{2+}$ plus) (TaKaRa), dNTP (TaKaRa), DEPC water, paraffin oil, 6×DNA loading buffer (including Sybr Green)

Instruments and materials: a home-built instrument for nucleic acid amplification (See Application CN201110456811.9); the reaction tube for nucleic acid amplification capable of controlling a circulation path of liquid of Example 1, a gel electrophoresis instrument, a gel imager (Bio-Rad)

Primers:

```
JxbUL54F1:
                                     (SEQ ID NO. 1)
GTGCGCCTTGACACTGTAC

JxbUL54R11:
                                     (SEQ ID NO. 2)
CGACAAGTACTTTGAGCAGG
```

Test template 1: DNA extract of CMV virus, and the concentration is $10^3$ copies/mL Test template 2: DEPC water 2. Experimental Method:

(1) Preparation of the amplification reagent: 3.2 mM dNTP, 4 μL 10× Fast Buffer I ($Mg^{2+}$ plus), 1 U SpeedSTAR HS DNA polymerase, 0.4 μL 10 μM JxbUL54F1, 0.4 μL 10 μM JxbUL54R11, 5 μL test template; and DEPC water is used to make up to a total volume of 40 μL.

(2) Amplification of nucleic acid: a. the amplification reagent prepared in (1) is injected into a reaction tube for nucleic acid amplification of the invention capable of controlling a circulation path of liquid, and 10 μl of paraffin oil is added dropwise and the region for nucleic acid amplification is allowed to be filled with the amplification reagent by centrifugation, vibration or other means; b. The bottom temperature of the home-built instrument for nucleic acid amplification is set to 95° C., the upper temperature is set to 60° C., and the amplification time is set to 30 minutes. The reaction tube containing the amplification reagent is introduced into the instrument for nucleic acid amplification, and the amplification procedure is started, and the reaction tube is taken out after the procedure is completed.

(3) Electrophoresis detection of amplified product: 5 μl of the amplified product is taken from the reaction tube and mixed with 1 μl loading buffer, and then subjected to 3% agarose gel electrophoresis for detection.

3. Experimental results: as shown in FIG. 4, lane 1 and lane 2 show amplification results of positive samples, and lane 3 and lane 4 show amplification results of negative control (DEPC water). As can be seen from the results, the reaction tube of the invention can enable the amplification of DNA templates; and there is no band observed in the negative control, indicating that no non-specific amplification occurs.

Example 3: Amplification and Detection of RNA Templates in the Reaction Tube for Nucleic Acid Amplification Capable of Controlling a Liquid Circulation Path of Example 1

1. Experimental Materials

Chemical reagents: SpeedSTAR HS DNA polymerase (TaKaRa), Reverse transcriptase MMLV (Transgen), 10× Fast Buffer I ($Mg^{2+}$ plus) (TaKaRa), dNTP (TaKaRa), DEPC water, paraffin oil, 6×DNA loading buffer (including Sybr Green)

Instruments and materials: a home-built instrument for nucleic acid amplification (See Application CN201110456811.9); the reaction tube for nucleic acid amplification capable of controlling a circulation path of liquid of Example 1, a gel electrophoresis instrument, a gel imager (Bio-Rad)

Primers:

```
CA16-WJ-F6-1:
                                     (SEQ ID NO. 3)
CAAGTAYTACCYACRGCTGCCAA

CA16-WJ-R6-1:
                                     (SEQ ID NO. 4)
CAACACACAYCTMGTCTCAATGAG
```

Test template 1: RNA extract of Coxsackievirus A16 (CA16 virus), concentration is $10^3$ copies/mL Test template 2: DEPC water 2. Experimental Method:

(1) Preparation of Amplification Reagent:

3.2 mM dNTP, 4 μL 10× Fast Buffer I ($Mg^{2+}$ plus), 1 U SpeedSTAR HS DNA polymerase, 0.4 U MMLV, 0.4 μL 10 μM JxbUL54F1, 0.4 μL 10 μM JxbUL54R11, 5 μl test template; and DEPC water is used to make up to a total volume of 40 μl.

(2) Amplification of nucleic acid: a. the amplification reagent prepared in (1) is injected into a reaction tube for nucleic acid amplification of the invention capable of controlling a circulation path of liquid, and 10 µl of paraffin oil is added dropwise and the region for nucleic acid amplification is allowed to be filled with the amplification reagent by centrifugation, vibration or other means; b. The temperature of the heating module at the bottom of the instrument is set to 60° C. for 20 minutes, and then set to 95° C. for 30 minutes; the temperature of the heating module at the top of the instrument is set to a constant temperature of 60° C. for 50 minutes. The reaction tube containing the amplification reagent is introduced into the instrument, and the amplification procedure is started, and the reaction tube is taken out after the procedure is completed.

(3) Electrophoresis detection of amplified product: 5 µl of the amplified product is taken from the reaction tube and mixed with 1 µl loading buffer, and then subjected to 3% agarose gel electrophoresis for detection.

3. Experimental results: as shown in FIG. 5, lane 1 and lane 2 show amplification results of positive samples, and lane 3 and lane 4 show amplification results of negative control (DEPC water). As can be seen from the results, the reaction tube of the invention can enable the amplification of RNA templates; and there is no band observed in the negative control, indicating that no non-specific amplification occurs.

Example 4: Comparison of the Consistency and Specificity Between the Amplifications in the Reaction Tubes with and without the Function of Circulation Control 1. Experimental Materials Chemical reagents: SpeedSTAR HS DNA polymerase (TaKaRa), 10× Fast Buffer I ($Mg^{2+}$ plus) (TaKaRa), dNTP (TaKaRa), DEPC water, paraffin oil, 6×DNA loading buffer (containing Sybr Green)

Instruments and materials: a home-built instrument for nucleic acid amplification; the reaction tube for nucleic acid amplification capable of controlling a circulation path of liquid of Example 1, a reaction tube without the function of circulation control (see application number 201110360350.5), a gel electrophoresis instrument, a gel imager (Bio-Rad)

Primers:

```
JxbUL54F1:
                                          (SEQ ID NO. 1)
GTGCGCCTTGACACTGTAC

JxbUL54R11:
                                          (SEQ ID NO. 2)
CGACAAGTACTTTGAGCAGG
```

Test template 1: DNA extract of CMV virus, and the concentration is $10^3$ copies/mL Test template 2: DEPC water 2. Experimental Method:

(1) Preparation of amplification reagent: 3.2 mM dNTP, 4 µL 10× Fast Buffer I ($Mg^2$ plus), 1 U SpeedSTAR HS DNA polymerase, 0.4 µL 10 µM JxbUL54F1, 0.4 µL 10 µM JxbUL54R11, 5 µl test template, and DEPC water is used to make up to a total volume of 40 µl.

(2) Amplification of nucleic acid: a. the amplification reagent prepared in (1) is injected into a reaction tube for nucleic acid amplification of the invention capable of controlling a circulation path of liquid, or the reaction tube without the function of circulation control, respectively. 10 µl of paraffin oil is added dropwise and the region for nucleic acid amplification is allowed to be filled with the amplification reagent by centrifugation, vibration or other means; b. the bottom temperature of the home-built instrument for nucleic acid amplification is set to 95° C., the upper temperature is set to 60° C., and the amplification time is set to 30 minutes. The reaction tubes containing the amplification reagent are introduced into the instrument, and the amplification procedure is started; and the reaction tube is taken out after the procedure is completed.

(3) Electrophoresis detection of amplified product: 5 µl of the amplified product is taken from the reaction tube and mixed with 1 µl loading buffer, and then subjected to 3% agarose gel electrophoresis for detection.

3. Experimental Results:

Lanes 1-4 in FIG. 6 show the amplification results of positive samples, wherein the bands from the samples amplified in the reaction tube for nucleic acid amplification capable of controlling a spontaneous circulation path of liquid of the invention (FIG. 6*a*) have a significantly stronger intensity than the bands from the samples amplified in the reaction tube without the function of controlling a circulation path (FIG. 6*b*). Lanes 5-8 in FIG. 6 show the amplification results of negative samples, wherein Lanes 5-8 in FIG. 6*a* show no bands on a clear background, indicating that no non-specific amplification such as primer dimer is produced in the samples amplified in the reaction tube capable of controlling a liquid circulation path of the invention; while the formation of primer dimers is clearly observed in the samples amplified in the reaction tube without the function of circulation control (FIG. 6*b*). The above results demonstrate that the reaction tube capable of controlling a spontaneous circulation path of liquid of the invention has a function of improving consistency and specificity of the amplification in different tubes.

Example 5: Comparison of Amplification Efficiency of Reaction Tubes with and without the Function of Circulation Control 1. Experimental Materials Chemical reagents: SpeedSTAR HS DNA polymerase (TaKaRa), 10× Fast Buffer I ($Mg^{2+}$ plus) (TaKaRa), dNTP (TaKaRa), DEPC water, paraffin oil, 6×DNA loading buffer (containing Sybr Green)

Instruments and materials: a home-built instrument for nucleic acid amplification; the reaction tube for nucleic acid amplification capable of controlling a circulation path of liquid of Example 1, a reaction tube without the function of circulation control (see, application number 201110360350.5), a gel electrophoresis instrument, a gel imager (Bio-Rad)

Primers:

```
JxbUL54F1:
                                          (SEQ ID NO. 1)
GTGCGCCTTGACACTGTAC

JxbUL54R11:
                                          (SEQ ID NO. 2)
CGACAAGTACTTTGAGCAGG
```

Test template 1: DNA extract of CMV virus, and the concentration is $10^3$ copies/mL Test template 2: DEPC water 2. Experimental Method:

(1) Preparation of amplification reagent: 3.2 mM dNTP, 4 µL 10× Fast Buffer I ($Mg^{2+}$ plus), 1 U SpeedSTAR HS DNA polymerase, 0.4 µL 10 µM JxbUL54F1, 0.4 µL 10 µM JxbUL54R11, 5 µl test template, and DEPC water is used to make up to a total volume of 40 µl.

(2) Amplification of nucleic acid: a. the amplification reagent prepared in (1) is injected into a reaction tube for nucleic acid amplification of the invention capable of controlling a circulation path of liquid, and the reaction tube without the function of circulation control, respectively. 10 µl of paraffin oil is added dropwise and the region for nucleic acid amplification is allowed to be filled with the amplification reagent by centrifugation, vibration or other means; b. the bottom temperature of the home-built instrument for nucleic acid amplification is set to 95° C., the upper temperature is set to 60° C., and the amplification time is set to 15 minutes, 20 minutes or 25 minutes. The reaction tubes containing the amplification reagent are introduced into the instrument, and the procedure is started; and the reaction tube is taken out after the procedure is completed.

(3) Electrophoresis detection of amplified product: 5 µl of the amplified product is taken from the reaction tube and mixed with 1 µl loading buffer, and then subjected to 3% agarose gel electrophoresis for detection.

3. Experimental Results:

amplification results obtained with the reaction tube for nucleic acid amplification capable of controlling a spontaneous circulation path of liquid of the invention are shown in FIG. 7a, and amplification results obtained with the reaction tube without the function of circulation control are shown in FIG. 7b. The results show that, when amplification is performed with the reaction tube of the invention, weak band can be observed in positive samples after 20 minutes of amplification, and after 25 minutes, a strong band can be observed in positive samples; while when amplification is performed with the reaction tube without the function of circulation control, a weak band can be observed in positive samples until 25 minutes after start of amplification. This demonstrates that the reaction tube of the invention can improve efficiency of amplification as compared with the previous convection PCR method.

Example 6: Comparison of Results of Real-Time Fluorescence Detection on Amplifications in Reaction Tubes with or without the Function of Circulation Control 1. Experimental Materials Chemical reagents: SpeedSTAR HS DNA polymerase (TaKaRa), 10× Fast Buffer I ($Mg^{2+}$ plus) (TaKaRa), dNTP (TaKaRa), DEPC water, paraffin oil Instruments and materials: a home-built instrument for nucleic acid amplification and real-time fluorescence detection (see application number CN201110456811.9); the reaction tube for nucleic acid amplification capable of controlling a circulation path of liquid of Example 1, a reaction tube without the function of circulation control (see, application number 201110360350.5)

Primers:

JxbUL54F1:
(SEQ ID NO. 1)
GTGCGCCTTGACACTGTAC

JxbUL54R11:
(SEQ ID NO. 2)
CGACAAGTACTTTGAGCAGG

Probe: JxbUL54P1: FAM-AGCCGGCTCCAAGTG-CAAG-BHQ-1 (SEQ ID NO.5)

Test template 1: template of DNA extract from CMV virus, and the concentration is $10^6$ copies/mL Test template 2: template of DNA extract from CMV virus, and the concentration is $10^5$ copies/mL Test template 3: DEPC water 2. Experimental Method:

(1) Preparation of amplification reagent: 3.2 mM dNTP, 4 µL 10× Fast Buffer I ($Mg^{2+}$ plus), 1 U SpeedSTAR HS DNA polymerase, 0.4 µL 10 µM JxbUL54F1, 0.4 µL 10 µM JxbUL54R11, 0.2 µL 10 µM JxbUL54P1, 5 µl test template, and DEPC water is used to make up to a total volume of 40 µl.

(2) Amplification of nucleic acid: a. the amplification reagent prepared in (1) is injected into a reaction tube for nucleic acid amplification of the invention capable of controlling a circulation path of liquid, and the reaction tube without the function of circulation control, respectively. 10 µl of paraffin oil is added dropwise and the region for nucleic acid amplification is allowed to be filled with the amplification reagent by centrifugation, vibration or other means; b. the bottom temperature of the home-built instrument for nucleic acid amplification is set to 95° C., the upper temperature is set to 60° C., and the amplification time is set to 30 minutes. The reaction tubes containing the amplification reagent are introduced into the home-built instrument for nucleic acid amplification and real-time fluorescence detection, and the procedure is started; and after the procedure is completed, the reaction tube is taken out and the data is analyzed.

Figure 8A:
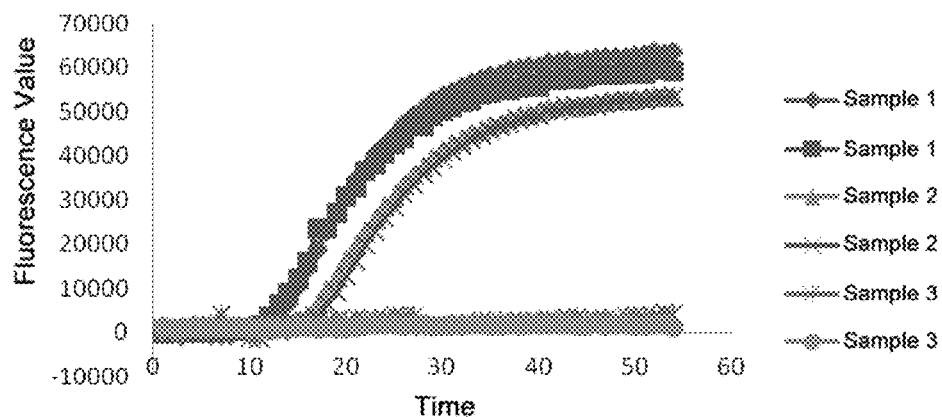
FIG. 8a shows the results of real time fluorescence detection of nucleic acid amplification in the reaction tube capable of controlling a spontaneous circulation path of liquid.
Figure 8B:
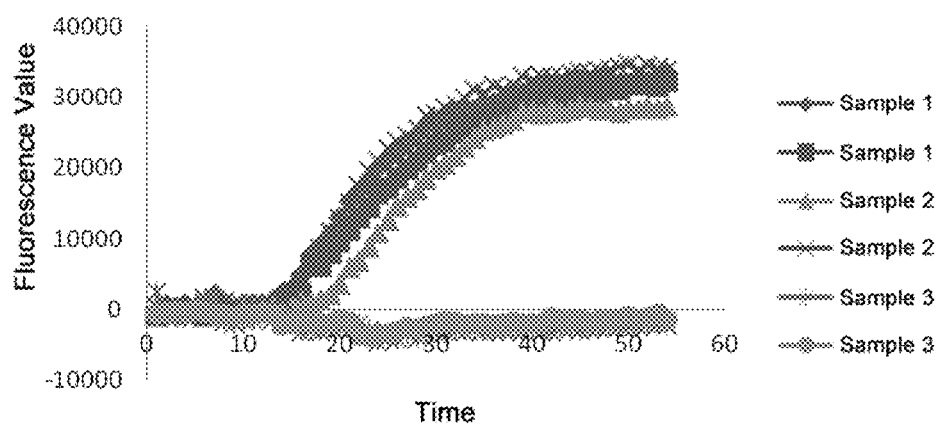
FIG. 8b shows results of real time fluorescence detection of nucleic acid amplification in the reaction tube without the function of circulation control.

3. Experimental Results:

Amplification results obtained with reaction tube for nucleic acid amplification capable of controlling a spontaneous circulation path of liquid of the invention are shown in FIG. 8a, and amplification results obtained with the reaction tube without the function of circulation control are shown in FIG. 8b. The results demonstrate that, when amplification is performed with the reaction tube of the invention, the repeatability of amplification curve of samples having the same concentration is obviously superior to the reaction tube without circulation control function, suggesting that the reaction tube for nucleic acid amplification capable of controlling a liquid circulation path of the invention can enable quantitative detection on nucleic acid sample.

While specific embodiments of the invention have been described in detail, those skilled in the art would understand that, according to all teachings that have been disclosed, various modifications and substitutions can be made to these details, which are within the scope of the invention. The full scope of the invention is given by the appended claims and any equivalents thereof.

The invention claimed is:

1. A reaction tube for nucleic acid amplification, comprising a tube body (1) with one end closed, said tube body (1) comprises a reservoir region (4) and a nucleic acid amplification region (3) located below the reservoir region, wherein an insert (2) is disposed in said nucleic acid amplification region (3) with an upper space remained above the insert (2) and a lower space remained below the insert (2), wherein when a reagent is injected into the reaction tube, the reagent is capable of moving along a circulation path through the upper space and the lower space in the reaction tube under an internal force or external force, due to a physical barrier effect of the insert (2).

2. The reaction tube of claim 1, wherein the insert (2) is provided along the central axis of the tube body (1), and both sides (a, b) of the insert are connected to the inner wall of the nucleic acid amplification region (3).

3. The reaction tube of claim 2, wherein the insert (2) divides the nucleic acid amplification region into a first region (3-1) and a second region (3-2) along the central axis of the tube body (1), and the first region (3-1) and the second region (3-2) are connected via the upper region (3-A) and the lower region (3-B) of the nucleic acid amplification region.

4. The reaction tube of claim 1, wherein the bottom of the tube body (1) is closed by means of a bottom plug (1-1) which cooperates with the tube body (1).

5. The reaction tube of claim 1, wherein the tube body (1) further comprises a tube cover cooperating therewith.

6. The reaction tube of claim 1, wherein the tube body (1) and the insert (2) are made of a heat-resistant material.

7. The reaction tube of claim 6, wherein the heat-resistant material is selected from, glass, polycarbonate, polypropylene, polyethersulfone and polysulfone.

8. A reaction apparatus for nucleic acid amplification, comprising the reaction tube according to claim 1 and one or more temperature controller capable of providing or removing heat, said temperature control controller is arranged outside or inside the reaction tube.

9. A kit, comprising the reaction tube according to claim 1.

10. The reaction tube of claim 1, wherein the reaction tube is characterized by any one or more of the following items:

(i) the distance between the lower end (d) of the insert (2) and the bottom of the tube body is greater than 0 mm and less than ½ of the height of the nucleic acid amplification region (3);

(ii) the distance between the upper end (c) of the insert (2) and the top of the nucleic acid amplification region (3) is greater than 0 mm and is less than ½ of the height of the nucleic acid amplification region (3);

(iii) the nucleic acid amplification region (3) having a height/inner diameter ratio of 3 to 12; and (iv) the nucleic acid amplification region (3) having a volume of 30 to 200 µl.

11. The reaction tube of claim 10, wherein the distance between the lower end (d) of the insert (2) and the bottom of the tube body is greater than 0 mm and less than ⅓ of the height of the nucleic acid amplification region (3); or, the distance between the lower end (d) of the insert (2) and the bottom of the tube body is greater than 0 mm and less than or equal to 4 mm.

12. The reaction tube of claim 10, wherein the distance between the upper end (c) of the insert (2) and the top of the nucleic acid amplification region (3) is greater than 0 mm and less than ⅓ of the height of the nucleic acid amplification region (3); or, the distance between the upper end (c) of the insert (2) and the top of the nucleic acid amplification region (3) is greater than 0 mm and less than or equal to 3 mm.

13. The reaction tube of claim 10, wherein the nucleic acid amplification region (3) has a height/inner diameter ratio of 6 to 9.

14. The reaction tube of claim 10, wherein the nucleic acid amplification region has a volume of 40 to 150 µl.

15. A method for amplifying a target nucleic acid in a sample, comprising using the reaction tube according to claim 1 or the reaction apparatus for nucleic acid amplification comprising the reaction tube according to claim 1.

16. The method of claim 15, comprising steps of:
1) injecting a reagent for nucleic acid amplification reaction into the reaction tube according to claim 1;
2) filling the reagent into the nucleic acid amplification region (3) by vibrating, centrifuging or other ways; and optionally, covering the surface of the reagent with a nonvolatile substance (or closing the reaction tube with a tube cover;
3) providing or removing heat at a specific site of the reaction tube by a temperature controller to conduct a RNA reverse transcription and/or DNA amplification reaction;
4) optionally, detecting the amplified product during or after nucleic acid amplification.

17. The method of claim 15, wherein the nucleic acid is DNA or RNA.

18. The method of claim 15, wherein the amplification is PCR reaction or reverse transcription reaction.

19. The method of claim 16, wherein the nonvolatile substance is paraffin oil or a low melting point wax.

* * * * *

SEQUENCE LISTING

<160> NUMBER OF SEQ ID NOS: 5

<210> SEQ ID NO 1
<211> LENGTH: 19
<212> TYPE: DNA
<213> ORGANISM: Artificial Sequence
<220> FEATURE:
<223> OTHER INFORMATION: synthetic primer -continued

```
<400> SEQUENCE: 1
gtgcgccttg acactgtac                                                    19

<210> SEQ ID NO 2
<211> LENGTH: 20
<212> TYPE: DNA
<213> ORGANISM: Artificial Sequence
<220> FEATURE:
<223> OTHER INFORMATION: synthetic primer

<400> SEQUENCE: 2
cgacaagtac tttgagcagg                                                   20

<210> SEQ ID NO 3
<211> LENGTH: 23
<212> TYPE: DNA
<213> ORGANISM: Artificial Sequence
<220> FEATURE:
<223> OTHER INFORMATION: synthetic primer

<400> SEQUENCE: 3
caagtaytac cyacrgctgc caa                                               23

<210> SEQ ID NO 4
<211> LENGTH: 24
<212> TYPE: DNA
<213> ORGANISM: Artificial Sequence
<220> FEATURE:
<223> OTHER INFORMATION: synthetic primer

<400> SEQUENCE: 4
caacacacay ctmgtctcaa tgag                                              24

<210> SEQ ID NO 5
<211> LENGTH: 19
<212> TYPE: DNA
<213> ORGANISM: Artificial Sequence
<220> FEATURE:
<223> OTHER INFORMATION: synthetic probe

<400> SEQUENCE: 5
agccggctcc aagtgcaag                                                    19
```